United States Patent
Ito (10) Patent No.: US 9,326,897 B2
(45) Date of Patent: May 3, 2016

(54) APPLICATOR-TYPE TAMPON WITH STRAND MEMBER HAVING A HOOK UNIT

(75) Inventor: Yukihiro Ito, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 285 days.

(21) Appl. No.: 14/007,286

(22) PCT Filed: Mar. 23, 2012

(86) PCT No.: PCT/JP2012/002041
§ 371 (c)(1),
(2), (4) Date: Dec. 9, 2013

(87) PCT Pub. No.: WO2012/127877
PCT Pub. Date: Sep. 27, 2012

(65) Prior Publication Data
US 2014/0088485 A1    Mar. 27, 2014

(30) Foreign Application Priority Data

Mar. 24, 2011   (JP) .................................. 2011-065990

(51) Int. Cl.
*A61F 13/20*    (2006.01)
*A61F 13/26*    (2006.01)
*A61F 13/32*    (2006.01)
*A61F 13/34*    (2006.01)

(52) U.S. Cl.
CPC ................. *A61F 13/34* (2013.01); *A61F 13/26* (2013.01); *A61F 13/266* (2013.01); *A61F 13/20* (2013.01)

(58) Field of Classification Search
CPC ...... A61F 13/20; A61F 13/202; A61F 13/204; A61F 13/2042; A61F 13/26; A61F 13/34
See application file for complete search history.

(56) References Cited

U.S. PATENT DOCUMENTS

| 3,139,886 | A | * | 7/1964 | Tallman | A61F 13/26 206/438 |
| 4,332,251 | A | * | 6/1982 | Thompson | A61F 13/26 604/16 |
| 6,679,868 | B2 | | 1/2004 | Kostadimas | |
| 2002/0095128 | A1 | | 7/2002 | Petit | |
| 2005/0090794 | A1 | * | 4/2005 | Dyer | A61F 13/34 604/385.18 |
| 2008/0033337 | A1 | * | 2/2008 | Dougherty, Jr. | A61F 13/266 604/15 |

FOREIGN PATENT DOCUMENTS

| DE | 202006016949 U1 | 3/2008 |
| EP | 2174629 A1 | 4/2010 |
| JP | 286591 | 7/1933 |

(Continued)

OTHER PUBLICATIONS

Office Action mailed Feb. 10, 2015, corresponding to Japanese patent application No. 2011-065990.

(Continued)

*Primary Examiner* — Lynne Anderson
*Assistant Examiner* — Kathryn E Ditmer
(74) *Attorney, Agent, or Firm* — Hauptman Ham, LLP (57) ABSTRACT

A sanitary tampon 10 includes an absorber 11 and a strand member 12 extending out from a tail end of the absorber 11 in a direction of insertion inside the vagina. A hook unit 20 is configured from a member different from the strand member 12 and distended outside from a circumferential surface 12e of the strand member 12 is provided in the strand member 12.

8 Claims, 6 Drawing Sheets

(56) References Cited

FOREIGN PATENT DOCUMENTS

| | | |
|---|---|---|
| JP | 52-136497 | 12/1976 |
| JP | 2001502929 A | 3/2001 |
| JP | 2002532199 A | 10/2002 |
| JP | 2004528870 A | 9/2004 |
| JP | 2008302115 A | 12/2008 |
| WO | 9806365 A1 | 2/1998 |
| WO | 0037013 A1 | 6/2000 |
| WO | 02058609 A2 | 8/2002 |
| WO | 2005044165 A1 | 5/2005 |

OTHER PUBLICATIONS

Extended European Search Report issued Aug. 21, 2014, corresponding to European patent application No. 12761278.6.
Corresponding International Application No. PCT/JP2012/002041 Search Report and Written Opinion dated Jun. 26, 2012.
Office Action dated Oct. 8, 2015, corresponding to European Patent Application No. 12761278.6.

* cited by examiner

APPLICATOR-TYPE TAMPON WITH STRAND MEMBER HAVING A HOOK UNIT

RELATED APPLICATIONS

The present application is based on, and claims priority from International Application Number PCT/JP2012/002041, filed Mar. 23, 2012 and Japanese Application Number 2011-065990, filed Mar. 24, 2011, the disclosure of which is hereby incorporated by reference herein in its entirety.

TECHNICAL FIELD

The present disclosure relates to a sanitary tampon and a tampon and applicator assembly in which an absorber can be taken out from inside the vagina via a strand member.

BACKGROUND ART

The sanitary tampon has an absorber that is disposed inside the vagina and absorbs the bodily fluid, and a strand member extending out from the absorber. When using the sanitary tampon, the user disposes the absorber at an appropriate position inside the vagina by using the applicator for tampon. At the time of use, the absorber absorbs the bodily fluid while being disposed inside the vagina. On the other hand, one end of the strand member is disposed inside the vagina along with the absorber while the other end is disposed outside the body. After use, the user takes out the absorber from inside the vagina by pulling the other end of the strand member (for example, see Patent Document 1 and Patent Document 2).

CITATION LIST

Patent Literature

PTL 1: Japanese Unexamined Patent Application Publication No. 2008-302115 (FIG. 2, etc.)
PTL 2: Japanese Unexamined Patent Application Publication (Translation of PCT Application) No. 2004-528870 (FIG. 1, etc.)

SUMMARY OF INVENTION

Technical Problem

However, the applicants faced the following problems as regard the above sanitary tampon.

The absorber is configured by compressing rayon and the like, and swells up by absorbing the bodily fluid inside the vagina. Therefore, in some cases it becomes difficult to take it out from inside the vagina after use. Therefore, when pulling out the absorber from inside the vagina after use, the user must pull the strand member by applying a relatively strong force. However, there is a case where it is difficult for the user to pull out the absorber due to slipping of the fingers holding the strand member and also due to the inability to apply sufficient force to the strand member.

Furthermore, for example, when pulling the absorber, if the proximity of the end that acts as the other end of the strand member is gripped, a space is generated between the fingers that act as the support and the absorber, and therefore, due to the force at the time of pulling out the absorber from inside the vagina, the absorber bounces to the proximity of the fingers that grip the strand member. If the absorber bounces to the proximity of the fingers that grip the strand member, the absorber after used may come in contact with the underwear or toilet bowl, and the underwear may get soiled.

Thus, the present invention has been made in view of the foregoing problem, and an objective thereof is to provide a sanitary tampon and a tampon and applicator assembly in which an absorber can be taken out easily and appropriately from inside the vagina.

Solution to Problem

A sanitary tampon according to the present invention includes: an absorber; and a strand member extending out from a tail end of the absorber in a direction of insertion inside the vagina, wherein a hook unit configured from a member different from the strand member and distended outside from a circumferential surface of the strand member is provided in the strand member.

Further, a sanitary tampon according to the present invention includes: an absorber; and a strand member extending out from a tail end of the absorber in a direction of insertion inside the vagina, the strand member is provided with a hook unit including a knot of the strand member, and the hook unit is disposed inside the inner tube while the absorber is contained in the outer tube.

Further, an tampon and applicator assembly according to the present invention includes: an outer tube which contains the sanitary tampon; and an inner tube configured such that it can be inserted inside the outer tube, wherein one side of the outer tube is provided with a push-out aperture by which the absorber is pushed out, and the other side thereof is provided with an insertion aperture in which the inner tube is inserted, and the inner tube is configured such that the absorber can be pushed out toward the outside from the push-out aperture due to its movement towards the inside of the outer tube.

Further, an tampon and applicator assembly according to the present invention includes: an outer tube which contains an absorber and a strand member extending out from a tail end of the absorber in a direction of insertion inside the vagina; and an inner tube configured such that it can be inserted inside the outer tube, in which one side of the outer tube is provided with a push-out aperture by which the absorber is pushed out, and the other side thereof is provided with an insertion aperture in which the inner tube is inserted, and the inner tube is configured such that the absorber can be pushed out toward the outside from the push-out aperture due to its movement towards the inside of the outer tube, the application-type tampon, wherein the strand member is provided with a hook unit including a knot of the strand member, and the hook unit is disposed inside the inner tube while the absorber is contained in the outer tube.

Further, a tampon and applicator assembly according to the present invention includes: an absorber; and a strand member extending out from a tail end of the absorber in a direction of insertion inside the vagina, wherein the strand member is provided with a hook unit including a knot of the strand member, and the length from the tail end of the absorber up to the end of the hook unit at the absorber side is equal to or less than half the length of the strand member extending out from the tail end of the absorber.

Advantageous Effects of Invention

According to the sanitary tampon and an tampon and applicator assembly of the present invention, because a hook unit that distends towards the outside from the circumferential surface of the strand member or a hook unit that includes knots is provided in the strand member, the strand member can be pulled by hooking fingers in the hook unit, and a relatively thin strand member can be pulled by applying force. Thus, even in cases when the absorber swells up after used and it may be difficult to take it out, the absorber can be easily and appropriately taken out from inside the vagina. Furthermore, the hook unit becomes an indicator of the portion that is to be gripped with the fingers. Thus, the user can take out the absorber by gripping the strand member at an appropriate position. The pulling out of the absorber by gripping the end of the strand member at the side that is estranged from the absorber can be prevented, and the contact of the absorber after used with the underwear and toilet bowl and thereby soiling of the underwear, etc., can be prevented.

DESCRIPTION OF EMBODIMENTS

Figure 1:
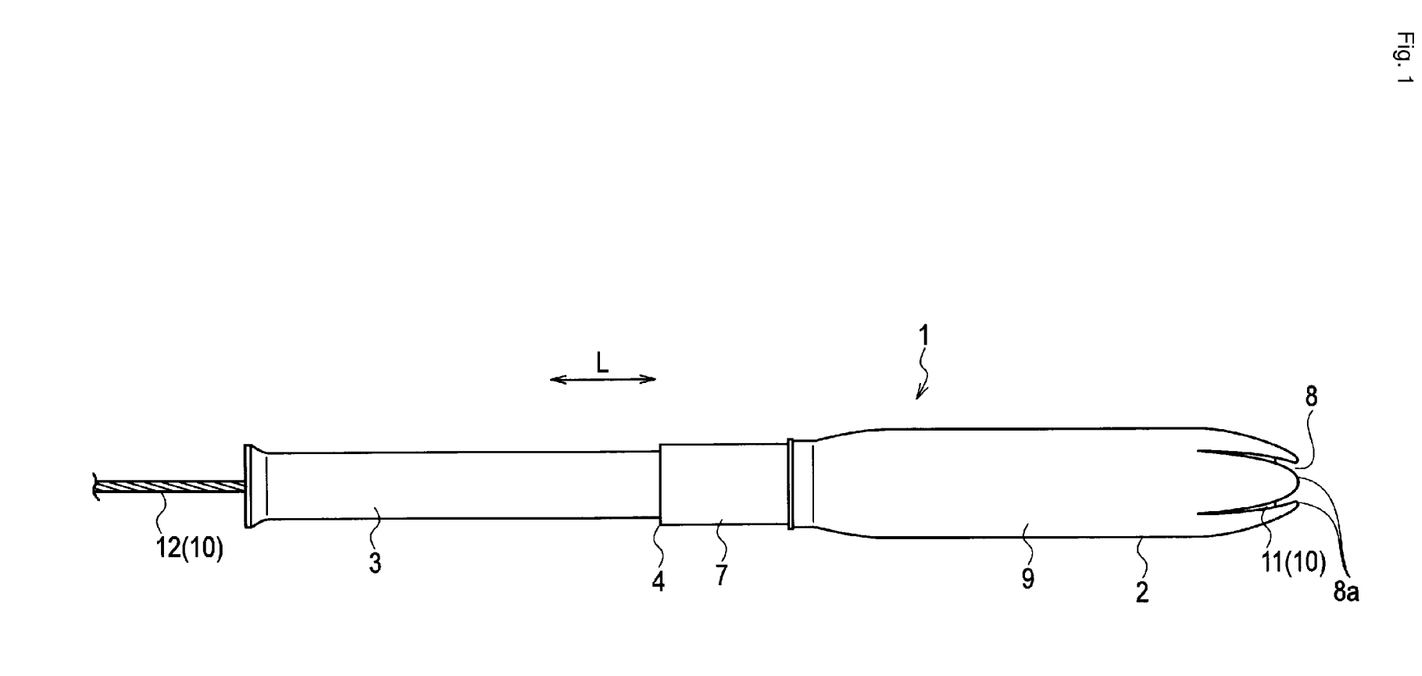
FIG. 1 is a plan view of a tampon and applicator assembly according to a first embodiment of the present invention.
Figure 2:
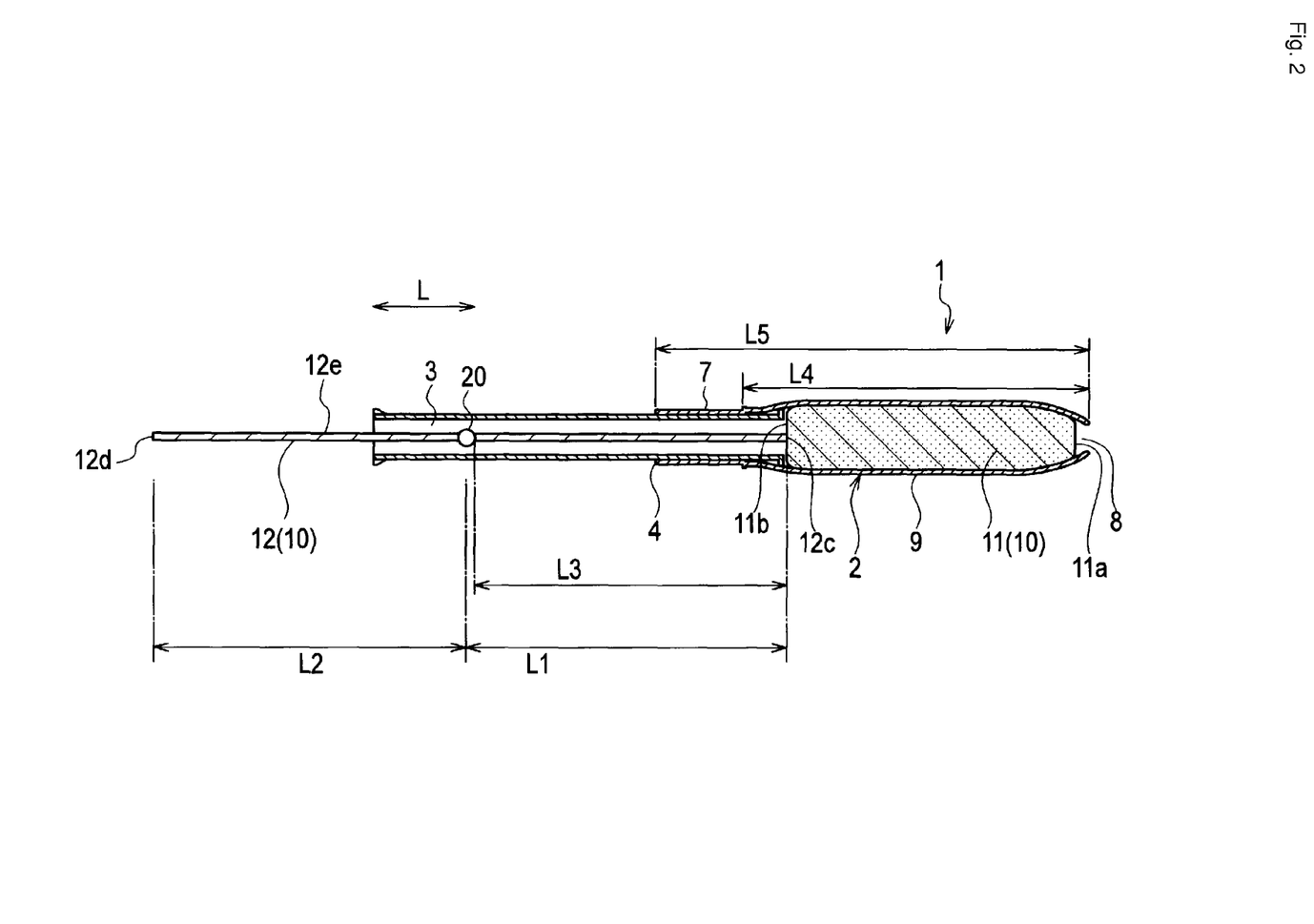
FIG. 2 is a cross-sectional view of the tampon and applicator assembly shown in FIG. 1.

A tampon and applicator assembly according to embodiments of the present invention is explained with reference to FIG. 1 and FIG. 2. FIG. 1 is a plan view showing the entire tampon and applicator assembly according to a first embodiment. FIG. 2 is a cross-sectional view of a cross section along a longitudinal direction L of the tampon and applicator assembly shown in FIG. 1.

A tampon and applicator assembly 1 includes an applicator for a tampon having an outer tube 2 and an inner tube 3, and a sanitary tampon 10 contained therein. The outer tube 2 and the inner tube 3 are cylindrical in shape having a hollow portion inside. The cross-sectional shape of the outer tube 2 and the inner tube 3 is a precise circle. The outer tube 2 and the inner tube 3 are entirely formed by polyolefins such as polyethylene and/or polypropylene, or by a cardboard whose surface is laminated with a polyolefin film. Although the cross-sectional shape of the outer tube 2 and the inner tube 3 according to the present embodiment is a precise circle, a shape that can be inserted easily inside the vagina, e.g., elliptical, may suffice as the cross-sectional shape of the outer tube 2 and the inner tube 3 according to some embodiments of the present invention.

An absorber 11 that configures the sanitary tampon 10 is contained inside the outer tube 2. The sanitary tampon 10 has the absorber 11 and a strand member 12 extending out from the absorber 11. The absorber 11 is positioned at a push-out aperture 8 side of the outer tube 2 that is described later, and has a tip 11a in the direction of insertion inside the vagina, and a tail end 11b in the direction of insertion inside the vagina. The strand member 12 is attached to the absorber 11 by sewing, hooking, or joining with an adhesive, etc. The strand member 12 is inserted inside the inner tube 3 from the tail end 11b of the absorber 11, and its ends are taken out from the inner tube 3. A strand tip 12c, which is the end of the strand member 12 at the absorber 11 side is fixed to the absorber 11, and a strand tail end 12d, which is the other end of the strand member 12 is the free end. The user can pull out the absorber 11 from inside the vagina by pulling the strand member 12 while the absorber 11 is disposed inside the vagina.

The absorber 11 is configured from a variety of liquid absorbent materials that are generally used in absorbent products, such as rayon, cotton, and synthetic fibers. Materials including creped cellulose wadding, textured synthetic fibers, foam, tissue, and tissue laminate, or similar materials, or a combination of similar materials can be illustrated as the other materials of the absorber 11.

The absorber 11 according to the present embodiment is formed by cutting a 2.0 g of nonwoven fabric sheet in which rayon and cotton have been mixed in the ratio of 8:2 into a fixed length, processing it into a roll shape, and then providing a spun bond nonwoven cloth of polypropylene on the outside in the form of a cover material.

The strand member 12 is used to take out the absorber 11 from inside the vagina safely and securely. The strand member 12 may be such that it has a strength that does not cause it to break when the absorber 11 disposed inside the vagina is pulled out, and specifically, it may be such that it has a strength that does not cause it to break when it is pulled with a force of 5 N or more. Spun yarn of synthetic fibers such as nylon and polyester, spun yarn of filament, cotton, or any other natural fiber, and spun yarn of regenerated fibers such as rayon can be illustrated as the material of the strand member 12. The strand member 12 according to the present embodiment is formed by twisting together eight No. 20 threads of PET material manufactured by Omikenshi Co., Ltd.

The strand member 12 is colored with red color No. 225. By thus coloring the strand member 12, the strand member 12 can be distinguished even in relatively dimly lit places such as toilets, and the visibility at the time of gripping can be improved.

The push-out aperture 8 from which the absorber 11 is pushed out is provided at one end (tip) of the outer tube 2. In the push-out aperture 8, a petal body 8a that is to be deformed radially outwards when the absorber 11 is pushed out is formed. The petal body 8a initially closes the push-out aperture 8, and when the absorber 11 is pushed out by the inner tube 3, the petal body 8a gets flared by the absorber 11 and opens up the push-out aperture 8. Thus, the absorber 11 is pushed out from the outer tube 2, and can be inserted inside the user's body.

On the other end, which is the tail end of the outer tube 2, an insertion aperture 4 in which the inner tube is inserted is formed. At the insertion aperture 4 side of the outer tube 2, a grip tube unit 7 that is held by fingers during the movement operation of the outer tube 2 and the inner tube 3 is provided. The grip tube unit 7 has a smaller diameter than the diameter of the outer tube main body 9 between the push-out aperture 8 and the grip tube unit 7. The tip portion of the inner tube 3 is inserted in the grip tube unit 7, and the tip surface of the inserted inner tube 3 faces the absorber 11.

Figure 3:
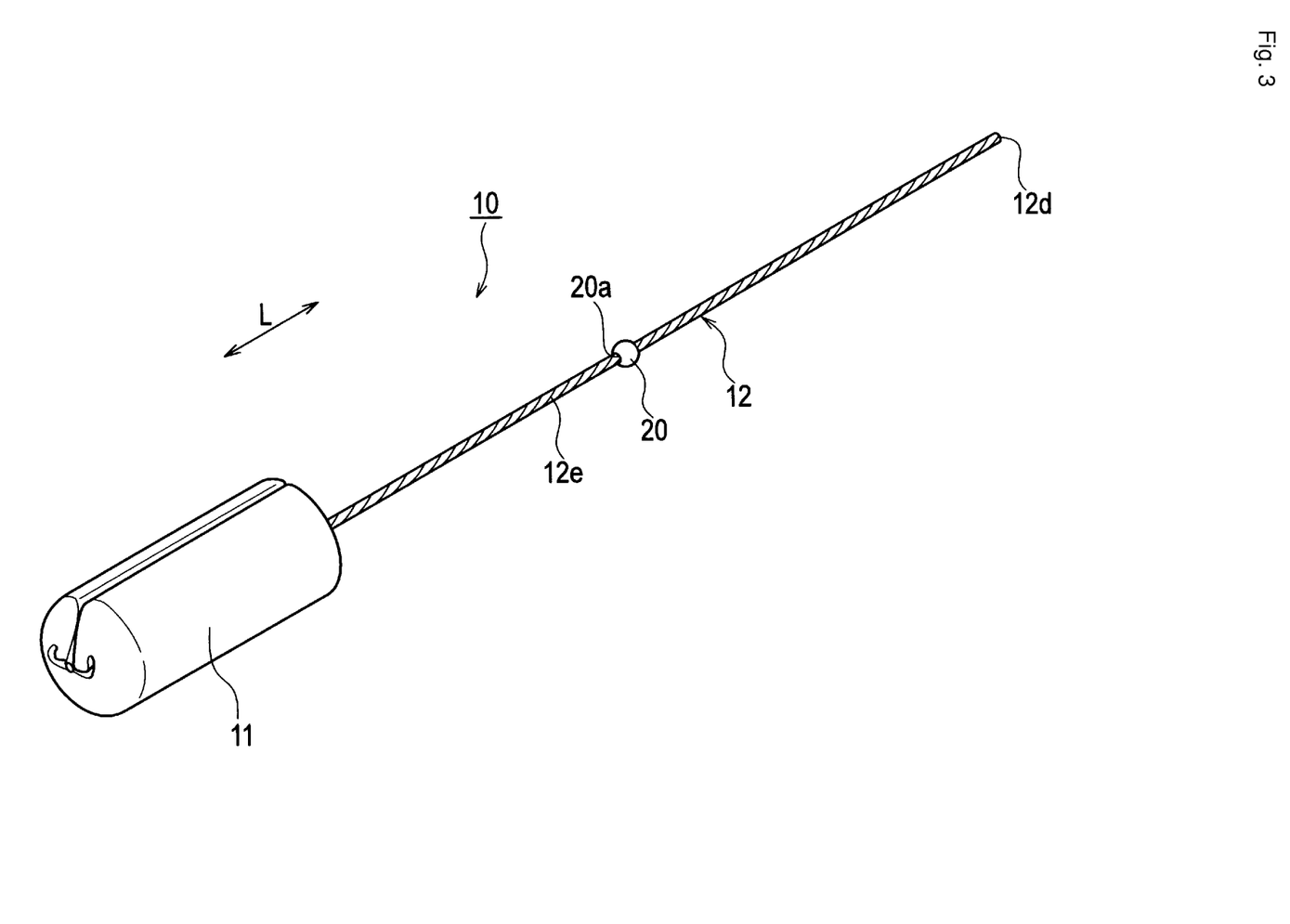
FIG. 3 is a perspective view of the sanitary tampon shown in FIG. 1.

A hook unit 20 that distends towards the outside from the circumferential surface 12e of the strand member 12 is provided in the strand member 12. The hook unit 20 is configured from a member different from the strand member 12. The hook unit 20 is a spherical bead and a through hole 20a is formed on its central line. The strand member 12 is inserted inside the through hole 20a of the hook unit 20. The hook unit 20 and the strand member 12 are fixed by an adhesive.

The hook unit 20 is formed from a molding such as a bead made from synthetic resin or from a hot melt adhesive. The hook unit 20 according to the present embodiment is formed from a plastic bead. The bead is spherical in shape. By configuring the hook unit 20 from a bead, for example, that protrudes outside from the circumferential surface 12e of the strand member 12, the fingers can be hooked easily when the strand member 12 is gripped. Furthermore, by configuring the hook unit 20 from an adhesive such as hot melt, the sliding of fingers gripping the strand member 12 can be made difficult when the absorber 11 is pulled via the strand member 12.

As shown in FIG. 2, when the absorber 11 is contained in the outer tube 2, the hook unit 20 is disposed inside the inner tube 3. For example, if the hook unit 20 is disposed outside the inner tube 3 when the absorber 11 is contained in the outer tube 2, the hook unit 20 is inserted inside the inner tube 3 when the absorber 11 is pushed out from the outer tube 2, and therefore, the hook unit 20 and the inner tube 3 get hooked, and it might become difficult to smoothly push out the absorber 11. However, by disposing the hook unit 20 inside the inner tube 3 when the absorber 11 is contained in the outer tube 2, the hooking of the inner tube 3 and the hook unit 20 when the absorber 11 is pushed out from the outer tube 2 can be prevented, and it becomes possible to smoothly push out the absorber 11.

The hook unit 20 is disposed such that the length L1 of the strand member 12 from the tail end 11b of the absorber 11 up to the center of the hook unit 20 is equal to or less than the length L2 from the strand tail end 12d of the strand member 12 up to the center of the hook unit 20. That is, the hook unit 20 is disposed in the proximity of the center in the longitudinal direction L of the strand member 12 (i.e., the longitudinal direction of the absorber 11 and the tampon and applicator assembly 1) or at the absorber side from the center. Furthermore, the length L3 from the tail end 11b of the absorber 11 up to the end of the hook unit 20 at the absorber side is equal to or less than half of the length L6 of the strand member 12. Due to the fact that the hook unit 20 is disposed at the absorber side from the center in the longitudinal direction of the strand member 12, the configuration can be made such that the fingers that act as the support and the absorber are not spaced out too much when the absorber 11 is pulled out by gripping the hook unit 20, and therefore, the force when the absorber 11 is pulled out from inside the vagina can be controlled, and bouncing of the absorber 11 up to the proximity of the fingers that grip the strand member 12 can be prevented. The contact of the absorber after used with the underwear and the toilet boil, thereby soiling of the underwear, etc., can be prevented.

Furthermore, for example, in a hook unit having a plurality of beads, etc., the center of the hook unit positioned at the extreme side of the absorber is desired to be positioned at the absorber side from the center of the strand member 12. By thus configuring the hook unit, the fingers that act as the support and the absorber 11 can be prevented from becoming too spaced out when no matter which bead is gripped and pulled.

In the present embodiment, the length of the strand member 12 that extends out from the tail end of the absorber is 140 mm, the length L1 of the strand member 12 from the absorber 11 up to the center of the hook unit 20 is 70 mm, and the length L2 from the strand tail end 12d of the strand member 12 up to the center of the hook unit 20 is 70 mm. Furthermore, the diameter of the hook unit 20 is 4 mm. Incidentally, the length of the strand member 12 that extends out from the tail end of the absorber may be 120 to 150 mm.

Furthermore, the length L3 from the tail end 11b of the absorber 11 up to the end of the hook unit 20 at the absorber 11 side (length from the strand tip 12c up to the end of the hook unit 20 at the absorber 11 side) is longer than the length L4 from the end of the grip tube unit 7 at the push-out aperture 8 side up to the push-out aperture 8 (length of the outer tube main body 9). When disposing the absorber 11 inside the vagina, the outer tube main body 9 of the outer tube 2 is inserted inside the vagina and the absorber 11 is pushed out inside the vagina. Therefore, by spacing out the absorber 11 and the hook unit 20 by the length of the outer tube main body 9 or more, the hook unit 20 can be disposed precisely outside the vaginal opening when the absorber 11 is disposed inside the vagina.

Additionally, the length L3 from the tail end 11b of the absorber 11 up to the end of the hook unit 20 at the absorber 11 side (length from the strand tip 12c up to the end of the hook unit 20 at the absorber 11 side) is longer than the length L5 of the outer tube 2. When disposing the absorber 11 inside the vagina, the outer tube main body 9 is inserted inside the vagina and the absorber 11 is pushed out inside the vagina while the grip tube unit 7 of the outer tube is gripped. Therefore, by spacing out the absorber 11 and the hook unit 20 by the length of the outer tube 2 or more, the hook unit 20 can certainly be disposed outside the vaginal opening when the absorber 11 is disposed inside the vagina, and the hook unit 20 and the vaginal opening can be spaced out by at least the length of the grip tube unit 7 or more. Thus, a space where the strand member 12 is held with the fingers can be provided between the hook unit 20 and the vaginal opening.

The outer circumferential shape of the hook unit 20 is desired to be curved. Note that the curved shape indicates that the configuration may be such that sharp angular portions are not included, and a linear shape may be included partially. By shaping the outer circumference of the hook unit 20 as curved, the feeling experienced by the user at the time of gripping the hook unit 20 can be mellowed down. Furthermore, when using a sanitary tampon, the strand member 12 and the hook unit 20 are arranged in the proximity of the vaginal opening. Thus, for example, if the hook unit 20 is sharp, the user may get an unpleasant feeling from the hook unit 20. However, due to the fact that the hook unit 20 has a curved shape, the feeling experienced by the user can be mellowed down.

Subsequently, a form of usage of a tampon and applicator assembly thus configured is explained. When using the absorber 11, the user inserts the outer tube 2 up to the appropriate position of the vagina. Due to pressing of the inner tube 3 towards the outer tube 2 side by the user after inserting the outer tube 2 up to a predetermined position inside the vagina, the absorber 11 is pushed out from the push-out aperture 8 of the outer tube 2, and the absorber 11 is disposed at an appropriate position inside the vagina. A part of the strand member 12 extending out from the absorber 11 extends outside the body from the vaginal opening. The hook unit 20 attached to the strand member 12 is disposed outside the body.

After use, by gripping the hook unit 20 provided in the strand member 12 and pulling it towards the outside of the body, the user is able to pull the absorber 11 by firmly gripping the strand member 12. Thus, the absorber 11 can be taken out from inside the vagina.

By providing the hook unit 20 in the strand member 12, the user can firmly grasp the strand member 12, and slipping and displacement of the fingers gripping the strand member 12 can be prevented.

Because the hook unit 20 is an indicator of the position for placing the fingers, the user can grip the hook unit 20 at an appropriate position and can pull out the absorber 11. First-time users who are not familiar with the usage of sanitary tampons might pull out the absorber 11 while gripping the proximity of the strand tail end 12d of the strand member 12 without understanding the indication of the position to be gripped with fingers. Due to the centrifugal force of the absorber 11, an absorber that has absorbed the menstrual blood might come in contact with the toilet bowl, or might get adhered to clothing such as pants and shorts thereby soiling the surrounding. However, by providing the hook unit 20, the recommended region of the gripping position at the time of pulling out the absorber 11 can be shown, and even first-time users can use the product assuredly.

Because the hook unit 20 protrudes outside from the circumferential surface 12e of the strand member 12, the hook unit 20 can be identified by feel even when the hook unit 20 is covered with pubic hair, for example, and the user cannot see it.

Figure 4:
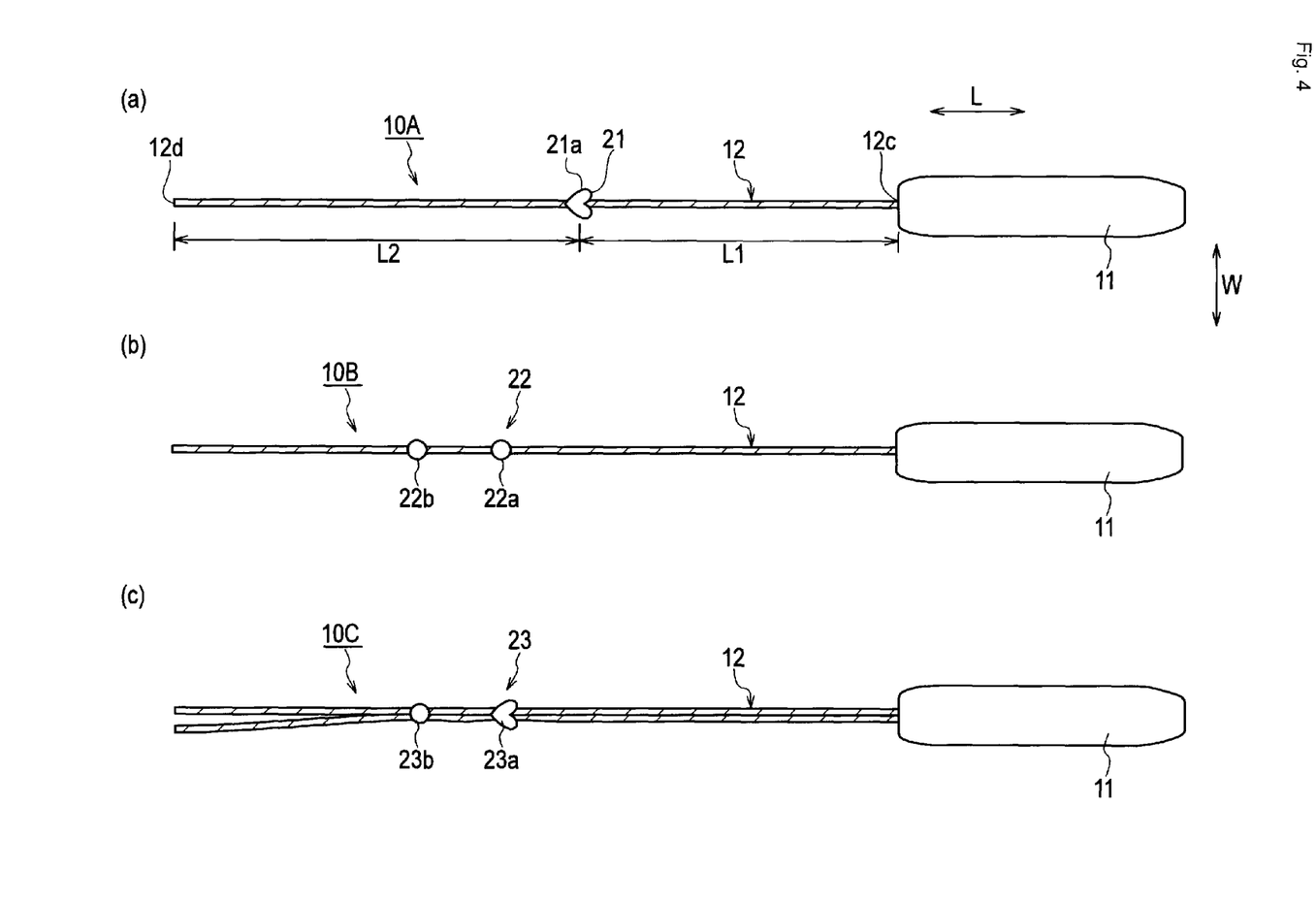
FIG. 4 is a plan view of a sanitary tampon according to modifications.

Note that the hook unit is not limited to the configuration according to the aforementioned embodiment, and various configurations can be adopted. Subsequently, the hook unit according to modifications is explained based on FIG. 4. Note that in the following explanation of the modifications, the description about the configuration same as the first embodiment is omitted. FIG. 4 shows the sanitary tampon according to the first modification through the third modification.

FIG. 4(a) is a plan view of a sanitary tampon 10A according to the first modification. A hook unit 21 of the sanitary tampon 10A according to the first modification is configured from a heart-shaped bead 21a. The length of the strand member 12 is 140 mm, the length L1 of the strand member 12 from the absorber 11 up to the center of the hook unit 21 is 65 mm, and the length L2 from the strand tail end 12d of the strand member 12 up to the center of the hook unit 21 is 75 mm. The length of the hook unit 21 in the longitudinal direction L is 8.7 mm, the length in the widthwise direction W that is perpendicular to the longitudinal direction L is 8.4 mm, and the thickness is 3.8 mm. By forming the hook unit 21 in various shapes, for example, a heart shape, such that a pattern is used as a motif, a medical device like a tampon can be beautified by the hook unit. Thus, the depressing feeling of the user associated with menstruation can be eased, and the willingness to use next time can be increased.

Furthermore, by adding a color to the hook unit, the decorative effect can be improved further. The color added to the hook unit is not particularly limited, for example, by adding a color according to the shape of the hook unit, such as red and pink color to a heart-shaped hook unit, the decorative effect can be improved further. Additionally, by coloring the hook unit, the hook unit can be distinguished, and the handling becomes easy particularly in dimly lit places, such as toilets.

As in the first modification, it is desired that the upper side of the heart shape of the heart-shaped hook unit be disposed at the absorber 11 side. According to such an arrangement, the fingers can be hooked easily when the strand member is pulled in the direction of estrangement from the absorber.

FIG. 4(b) is a plan view of a sanitary tampon 10B according to a second modification. A hook unit 22 of the sanitary tampon 10B according to the second modification is configured from spherical-shaped beads 22a and 22b. A plurality of beads 22a and 22b are disposed at a fixed interval along the longitudinal direction L of the strand member 12.

By providing a plurality of beads 22a and 22b, for example, even if the fingers slip while gripping one bead, the fingers can be hooked to the other bead. Furthermore, by disposing the beads such that a plurality of beads 22a and 22b can be gripped (the interval between the beads is made smaller than the width of the ball of a finger), the plurality of beads and fingers are in contact simultaneously, and therefore, slipping is made further difficult. Furthermore, by providing a plurality of beads, the user can pull out the absorber by gripping the portion that she can hold easily, and the operability can be improved.

FIG. 4(c) is a plan view of a sanitary tampon 10C according to a third modification. A hook unit 23 of the sanitary tampon 10C according to the third modification is configured from a heart-shaped bead 23a and a hemispherically-shaped bead 23b. Thus, the hook unit can also be configured by arranging a plurality of different beads.

Second Embodiment

Figure 5:
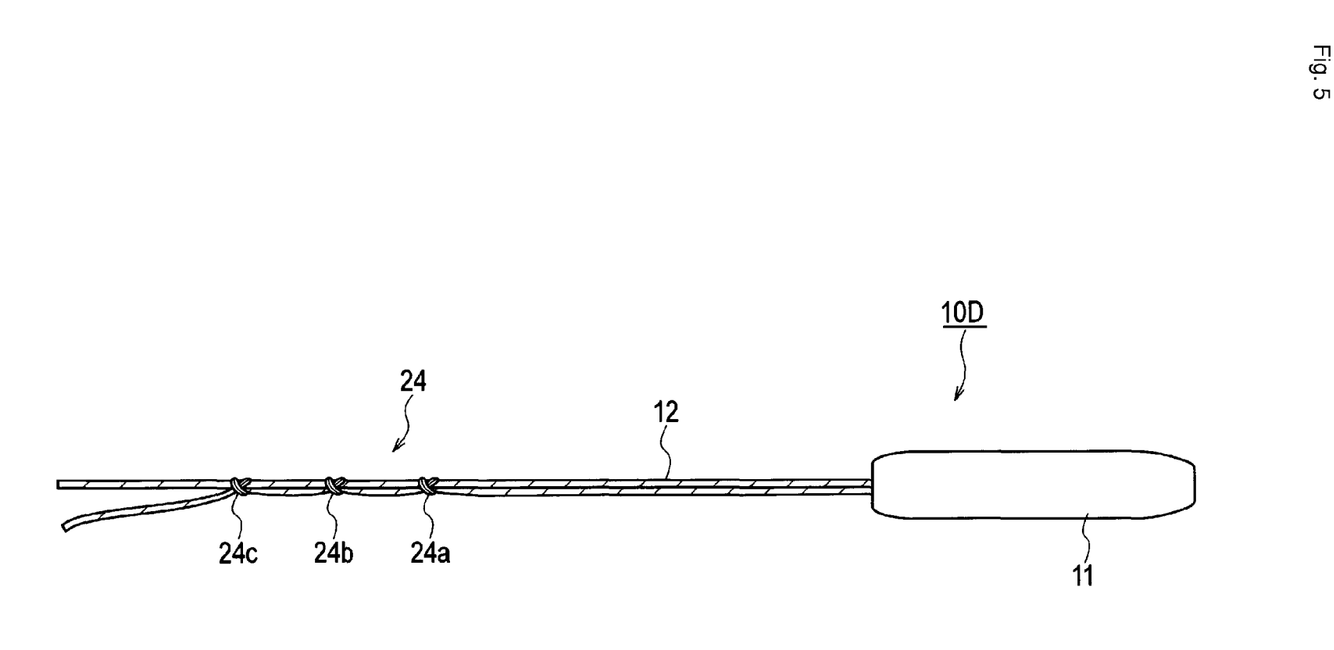
FIG. 5 is a plan view of a sanitary tampon according to a second embodiment.

Subsequently, a sanitary tampon according to a second embodiment is explained based on FIG. 5. A hook unit 24 of a sanitary tampon 10D according to the second embodiment is configured from the knots 24a, 24b, and 24c of the strand member 12. The diameter of the knots configuring the hook unit 24 is 2 mm.

By configuring the hook unit 24 from a plurality of knots 24a, 24b, and 24c, even when the fingers gripping the strand member slip, the fingers are hooked in the knots 24a, 24b, and 24c provided together, and therefore, the state in which strand member is gripped can be maintained. Furthermore, because the hook unit 24 can be configured from the strand member itself, beads, etc., become unnecessary, and therefore, the number of components can be reduced and the manufacturing process can be simplified.

Figure 6:
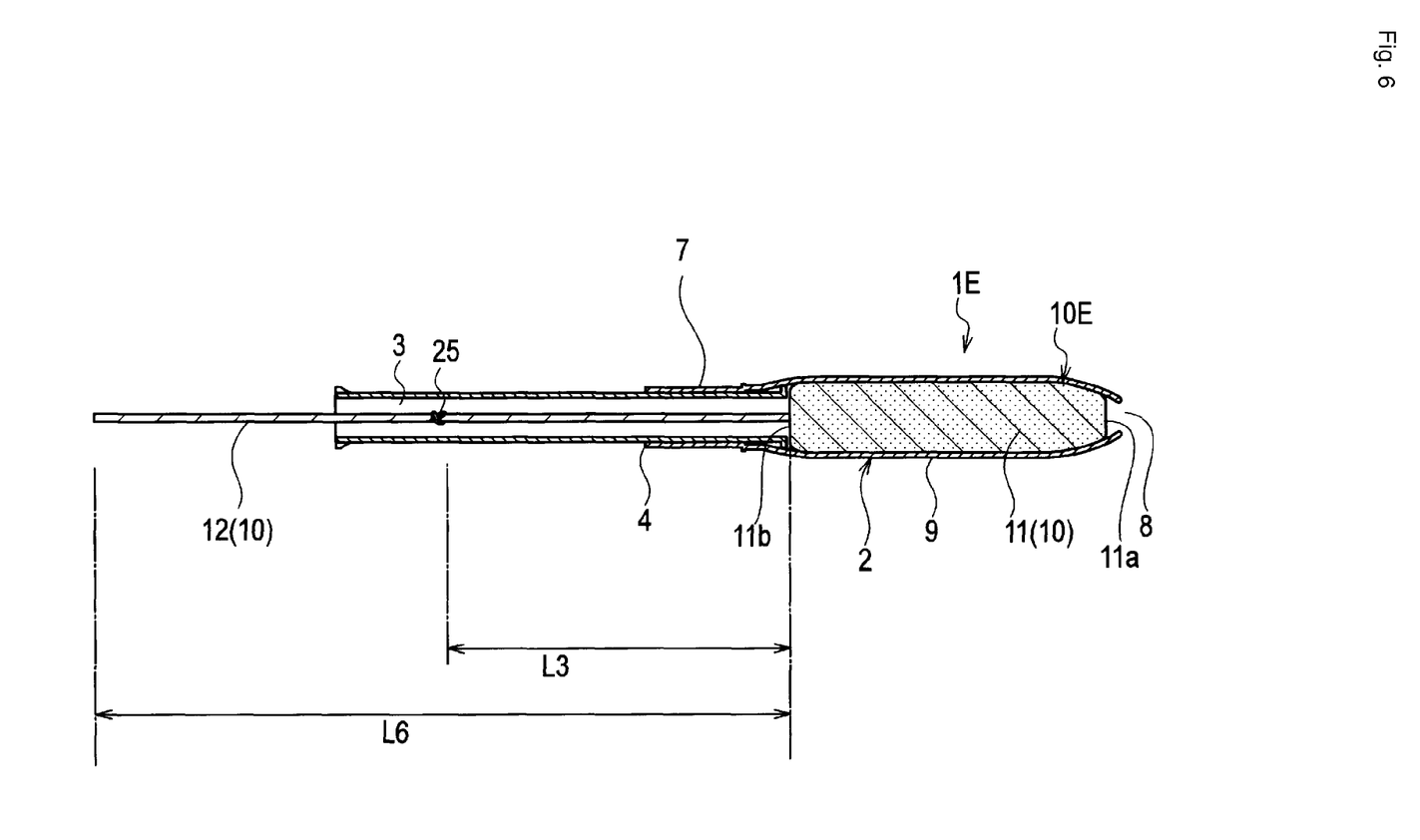
FIG. 6 is a cross-sectional view of a tampon and applicator assembly according to a fourth modification.

Note that a hook unit including knots is not limited to the configuration according to the aforementioned embodiment, and various configurations can be adopted. Subsequently, the hook unit according to a modification is explained based on FIG. 6. Note that in the following explanation of the modification, the description about the configuration same as the second embodiment is omitted. FIG. 6 shows a tampon and applicator assembly 1E having a sanitary tampon 10E according to a fourth modification.

The tampon and applicator assembly 1E according to the fourth modification contains the sanitary tampon 10E in which a hook unit 25 is provided. The hook unit 25 is configured from one knot 25a of the strand member 12. The knot 25a is disposed inside the inner tube 3 while the absorber 11 is contained in the outer tube 2. Furthermore, the length L3 from the tail end 11b of the absorber 11 up to the end of the hook unit 25 at the absorber side is equal to or less than half of the length L6 of the strand member 12.

By thus disposing the hook unit 25 inside the inner tube 3 when the absorber 11 is contained in the outer tube 2, the hooking of the inner tube 3 and the hook unit 25 when the absorber 11 is pushed out from the outer tube 2 can be prevented, and it becomes possible to smoothly push out the absorber 11. Furthermore, the length L3 from the tail end 11b of the absorber 11 up to the end of the hook unit 25 at the absorber side is equal to or less than half of the length L6 of the strand member 12, and because the hook unit is disposed in the proximity of the vaginal opening while the absorber 11 is disposed inside the vagina, the fingers that act as the support when the absorber is pulled out and the absorber can be disposed close to each other. Thus, the force at the time of pulling out the absorber 11 from inside the vagina is controlled, and bouncing of the absorber 11 up to the proximity of the fingers gripping the strand member 12 can be prevented. The contact of the absorber after used with the underwear and the toilet boil, and thereby soiling of the underwear, etc., can be prevented.

Thus, needless to say, the present invention includes various embodiments not described herein. Therefore, the technical range of the present invention is to be defined only by the inventive specific matter according to the adequate claims from the above description.

For example, the sanitary tampon may be contained inside the applicator for tampon and may be inserted inside the vagina by using the applicator for tampon, or may not be contained in the applicator for tampon and may be inserted inside the vagina by the fingers of the user.

MODE OF EXAMPLE

First Mode of Example

As for a first mode of example, Examples and a Comparative Example are illustrated, in which the pull resistance value of the hook unit of the present invention was measured. Note that the present invention is not limited thereto.

By using a strand member that does not have a hook unit and strand members according to Example 1 through Example 14 that have a hook unit, the strand member was gripped with fingers and pulled, and the resistance value at which the state in which the fingers did not slip could be maintained was investigated.

(Method of Measuring the Resistance Value)

The strand member according to the above embodiments are doubled up, and the hook unit is disposed such that the end of the hook unit is positioned at a portion that is 70 mm from the folded portion. A hook is attached at the tip of a digital force gauge model No. FGP-5 manufactured by SHIPO Corporation, and the bent portion of the strand member is hooked on to this hook. A portion that was 50 mm from the bent portion was gripped and pulled in a direction away from the hook, and when the hand slipped, the load at the time the strand member 12 slipped away from the hand was measured as the resistance value. The number of monitored persons was five. In each Example and Comparative Example, the resistance value was measured by five monitored persons.

The hook units according to the Example 1 through the Example 5 are configured from one knot or bead. The hook unit according to the Example 1 is configured from a knot. The hook unit according to the Example 2 is configured from a bead. The hook unit according to the Example 3 is configured from a bead that is larger than that of the hook unit according to the Example 2. The hook unit according to the Example 4 is configured from a heart-shaped bead according to the first modification. The hook unit is disposed such that the upper side of the heart shape faces the bent portion. The hook unit according to the Example 5 is configured from a heart-shaped bead according to the first modification. The hook unit is disposed such that the lower side of the heart shape faces the bent portion.

The hook unit according to the Example 6 is configured from an adhesive. The hook unit according to the Example 7 and the Example 8 is configured from a combination of one knot and one bead. The knot is disposed at the hook unit side and the bead is disposed adjoining to the knot. The distance between the center of the knot and the center of the bead is 30 mm. The bead of the hook unit according to the Example 7 is heart shaped and the bead of the hook unit according to the Example 8 is sphere shaped.

The hook unit according to the Example 9 through the Example 11 is configured from three knots, and the interval between the knots is different for each hook unit. In the hook unit according to the Example 9, the distance between the centers of adjoining knots is 5 mm. In the hook unit according to the Example 10, the distance between the centers of adjoining knots is 10 mm. In the hook unit according to the Example 11, the distance between the centers of adjoining knots is 15 mm.

The hook unit according to the Example 12 through the Example 14 is configured from three spherical-shaped beads, and the interval between beads is different for each hook unit. In the hook unit according to the Example 12, the distance between the centers of adjoining beads is 5 mm. In the hook unit according to the Example 13, the distance between the centers of adjoining beads is 10 mm. In the hook unit according to the Example 14, the distance between the centers of adjoining beads is 15 mm.

(Measurement Results)

The measurement results are shown in Table 1.

Note that the measurement results could not be acquired from the monitored person No. 3 for the Example 6, and the measurement results of all the monitored persons could be acquired for the other Examples.

TABLE 1

| | Comparative Example | Example 1 | Example 2 | Example 3 | Example 4 | Example 5 | Example 6 | Example 7 | Example 8 |
|---|---|---|---|---|---|---|---|---|---|
| n = 1 | 6.78 | 10.67 | 16.03 | 36.09 | 30.31 | 26.74 | 13.49 | 25.48 | 37.41 |
| n = 2 | 8.44 | 16.25 | 22.82 | 24.75 | 38.01 | 32.02 | 16.69 | 21.86 | 31.76 |
| n = 3 | 5.63 | 8.96 | 13.41 | 17.44 | 18.03 | 13.79 | — | 10.04 | 15.09 |
| n = 4 | 12.25 | 14.56 | 16.34 | 30.03 | 25.09 | 23.03 | 16.95 | 16.65 | 18.12 |
| n = 5 | 16.51 | 17.5 | 34.26 | 47.67 | 49.72 | 40.56 | 21.83 | 26.09 | 50 or more |
| Average | 9.92 | 13.59 | 20.57 | 31.20 | 32.23 | 27.23 | 13.79 | 20.02 | 20.48 |

| | Example 9 | Example 10 | Example 11 | Example 12 | Example 13 | Example 14 |
|---|---|---|---|---|---|---|
| n = 1 | 13.95 | 10.97 | 10.01 | 30.35 | 23.03 | 21.54 |
| n = 2 | 15.61 | 13.4 | 14.33 | 27.93 | 25.29 | 25.86 |
| n = 3 | 5.89 | 5.05 | 5.33 | 7.92 | 9.77 | 9.43 |
| n = 4 | 12.44 | 10.77 | 11.06 | 19.65 | 20.33 | 18.48 |
| n = 5 | 17.73 | 15.32 | 14.94 | 31.59 | 27.65 | 26.32 |
| Average | 13.12 | 11.10 | 11.13 | 23.49 | 21.21 | 20.33 |

(Unit: N)

It was understood that as compared to the strand member according to the Comparative Example, the strand member according to the Example 1 through the Example 9 and the Example 12 through the Example 14 had a higher resistance value as measured by all of the five monitored persons, and the fingers gripping the strand member did not slip easily. On the other hand, the resistance value of the strand member as measured by two of the five monitored persons according to the Example 10 and the Example 11 is higher than the Comparative Example, but that as measured by three monitored persons was lower than the Comparative Example. In the strand member according to the Example 10 and the Example 11, a plurality of knots are formed, and the interval between the knots is 10 mm or more. If the interval between the knots is 10 mm or more, the monitored persons regard that the plurality of knots cannot be gripped simultaneously and the resistance value becomes low. However, as in the strand member according to the Example 9, if the interval between the knots is 5 mm, it is regarded that the plurality of knots can be gripped simultaneously and the resistance value increases. Thus, when the hook unit is configured from a plurality of knots, it is desired that the knots be disposed such that the plurality of knots can be gripped in one go.

Second Mode of Example

As for a second mode of example, the sanitary tampon according to the present invention was inserted by using the applicator for tampon, and the position of the sanitary tampon inside the vagina was measured.
(Measurement Conditions)
In the sanitary tampon, the length of the absorber in the longitudinal direction is 45 mm and the length of the strand member in the longitudinal direction is 140 mm. The sanitary tampon was inserted inside the vagina by using the applicator for tampon according to the present embodiment, and the length L11 of the strand member extending out from the vaginal opening, the length L12 of the strand member disposed inside the vagina, and the length L13 from the tip of the absorber up to the vaginal opening was measured. The number of monitored persons was eight.
(Measurement Results)
The measurement results are shown in Table 2.

TABLE 2

|  | n = 1 | n = 2 | n = 3 | n = 4 | n = 5 | n = 6 | n = 7 | n = 8 | Average |
|---|---|---|---|---|---|---|---|---|---|
| L11 | 95 | 120 | 110 | 100 | 100 | 100 | 100 | 100 | 103.13 |
| L12 | 45 | 20 | 30 | 40 | 40 | 40 | 40 | 40 | 36.88 |
| L13 | 90 | 65 | 75 | 85 | 85 | 85 | 85 | 85 | 81.88 |

(Unit: mm)

From the above measurement results, the length of the sanitary tampon disposed inside the vagina (length from the tip of the absorber up to the vaginal opening) is between 65 mm and 90 mm. Thus, the hook unit is desired to be provided at a position that is spaced out by 90 mm or more from the tip of the absorber. Furthermore, the length of the absorber in the longitudinal direction differs according to the absorption performance, and the general length is between 30 mm and 70 mm. That is, the length from the strand tip of the strand member up to the vaginal opening differs according to the length of the absorber. Thus, it is desired that the position of the hook unit be adjusted according to the length of the absorber.

Furthermore, if the hook unit and the vaginal opening come closer while the absorber is disposed inside the vagina, it may become difficult to grasp the hook unit. Generally, when the hook unit is gripped, the hook unit and the strand member are gripped by at least two fingers. Thus, the hook unit and the vaginal opening are desired to be spaced out by as much distance in which at least the fingers can be disposed. On the other hand, if the hook unit and the vaginal opening are too far, the fingers that act as the support and the absorber will be spaced out, which is not desirable. From such a viewpoint, the distance between the hook unit and the vaginal opening is desired to be 30 mm or less. Therefore, the length from the strand tip up to the hook unit is desired to be in the range of 50 mm to 75 mm.

When the length from the strand tip up to the hook unit is in the range of 50 mm to 75 mm, the length from the tail end of the absorber up to the end of the hook unit at the absorber side is almost half the length of the strand member extending out from the tail end of the absorber. For example, by disposing the hook unit at the absorber side from the center in the longitudinal direction of the strand member, the strand at the tail end side from the hook unit can be grasped in the palm while the hook unit is gripped with fingers, and the strand member can be gripped firmly at a plurality of locations and pulled. Furthermore, if the length of the strand member extending out from the body, when the absorber is disposed inside the vagina, is too short, the strand member is covered inside body hair, and it may be difficult to grasp the strand member. On the other hand, if the length of the strand member extending out from the body, when the absorber is disposed inside the vagina, is too long, the strand member may come out from the underwear. From such a viewpoint, the length of the strand member is desired to be approximately 80 mm to 200 mm, and the more preferable length is approximately 100 mm to 160 mm.

This application claims the benefit of Japanese Application No. 2011-065990 the entire disclosure of which is incorporated by reference herein.

The invention claimed is:
1. An applicator-type tampon, comprising:
an outer tube;
an absorber contained in the outer tube;
a strand member extending out from a tail end of the absorber in a direction adapted to be oriented towards an outside of a vagina of a wearer in use;
a grip tube unit configured to be gripped by the wearer in use;
an inner tube insertable inside the outer tube; and
a hook unit extending outwardly from a circumferential surface of the strand member and disposed inside the inner tube while the absorber is contained in the outer tube,
wherein
one end of the outer tube is provided with a push-out aperture through which the absorber is configured to be pushed out, and the other end of the outer tube is provided with an insertion aperture in which the inner tube is inserted,
the inner tube is configured to push the absorber out of the outer tube from the push-out aperture due to a movement of the inner tube towards an inside of the outer tube,
the hook unit has first and second ends, the first end of the hook unit being closer to the absorber than the second end of the hook unit,
the grip tube unit is formed around the insertion aperture of the outer tube and has first and second ends, the first end of the grip tube unit being closer to the push-out aperture than the second end of the grip tube unit, and a length of the strand member from the tail end of the absorber up to the first end of the hook unit when the hook unit is disposed inside the inner tube is longer than a length from the first end of the grip tube unit up to the push-out aperture.

2. The applicator-type tampon according to claim 1, wherein the hook unit is configured to be hooked and pulled by a finger of the wearer to remove the absorber from the vagina of the wearer.

3. The applicator-type tampon according to claim 2, wherein the hook unit is a plastic bead.

4. The applicator-type tampon according to claim 2, wherein the hook unit is formed of hot melt adhesive.

5. The applicator-type tampon according to claim 2, wherein the hook unit has a plurality of beads with different shapes.

6. An applicator-type tampon, comprising:
an outer tube;
an absorber contained in the outer tube;
a strand member extending out from a tail end of the absorber in a direction adapted to be oriented towards an outside of a vagina of a wearer in use;
an inner tube insertable inside the outer tube; and
a hook unit extending outwardly from a circumferential surface of the strand member and disposed inside the inner tube while the absorber is contained in the outer tube,
wherein
one end of the outer tube is provided with a push-out aperture by which the absorber is configured to be pushed out, and the other end of the outer tube is provided with an insertion aperture in which the inner tube is configured to be inserted,
the inner tube is configured to push the absorber out of the outer tube from the push-out aperture due to a movement of the inner tube towards an inside of the outer tube,
the hook unit has first and second ends, the first end being closer to the absorber than the second end, and
a length of the strand member from the tail end of the absorber up to the first end of the hook unit when the hook unit is disposed inside the inner tube is longer than a length of the outer tube.

7. An applicator-type tampon, comprising:
an outer tube;
an absorber contained in the outer tube;
a strand member extending out from a tail end of the absorber in a direction adapted to be oriented towards an outside of a vagina of a wearer in use;
a grip tube unit configured to be gripped by the wearer when in use; and
an inner tube insertable inside the outer tube;
wherein
one end of the outer tube is provided with a push-out aperture by which the absorber is configured to be pushed out, and the other end of the outer tube is provided with an insertion aperture in which the inner tube is configured to be inserted, and
the inner tube is configured to push the absorber out of the outer tube from the push-out aperture due to a movement of the inner tube towards an inside the outer tube,
the strand member has a knot defining a hook unit,
the hook unit is disposed inside the inner tube while the absorber is contained in the outer tube,
the hook unit has first and second ends, the first end being closer to the absorber than the second end,
the grip tube unit is formed around the insertion aperture of the outer tube and has first and second ends, the first end of the grip tube unit being closer to the push-out aperture than the second end of the grip tube unit, and
a length of the strand member from the tail end of the absorber up to the first end of the hook unit when the hook unit is disposed inside the inner tube is longer than a length from the first end of the grip tube unit up to the push-out aperture.

8. An applicator-type tampon, comprising:
an outer tube;
an absorber contained in the outer tube;
a strand member extending out from a tail end of the absorber in a direction adapted to be oriented towards an outside of a vagina of a wearer in use; and
an inner tube insertable inside the outer tube;
wherein
one end of the outer tube is provided with a push-out aperture by which the absorber is configured to be pushed out, and the other end of the outer tube is provided with an insertion aperture in which the inner tube is configured to be inserted, and
the inner tube is configured to push the absorber out of the outer tube from the push-out aperture due to a movement of the inner tube towards an inside the outer tube,
the strand member has a knot defining a hook unit,
the hook unit is disposed inside the inner tube while the absorber is contained in the outer tube,
the hook unit has first and second ends, the first end being closer to the absorber than the second end, and
a length of the strand member from the tail end of the absorber up to the first end of the hook unit when the hook unit is disposed inside the inner tube is longer than the length of the outer tube.

* * * * *